(12) United States Patent
Hiyama et al.

(10) Patent No.: US 8,802,862 B2
(45) Date of Patent: Aug. 12, 2014

(54) 1,2-BENZISOTHIAZOL-3-ONE COMPOUND PRODUCTION METHOD

(75) Inventors: Takehiro Hiyama, Kako-gun (JP); Ichiro Yokoe, Osaka (JP); Takeshi Takeuchi, Kako-gun (JP); Michio Suzuki, Kako-gun (JP)

(73) Assignee: Sumitomo Seika Chemicals Co., Ltd., Kako-gun (JP)

( * ) Notice: Subject to any disclaimer, the term of this patent is extended or adjusted under 35 U.S.C. 154(b) by 0 days.

(21) Appl. No.: 14/003,086

(22) PCT Filed: Feb. 22, 2012

(86) PCT No.: PCT/JP2012/054252
§ 371 (c)(1),
(2), (4) Date: Sep. 4, 2013

(87) PCT Pub. No.: WO2012/127969
PCT Pub. Date: Sep. 27, 2012

(65) Prior Publication Data
US 2013/0345433 A1 Dec. 26, 2013

(30) Foreign Application Priority Data
Mar. 18, 2011 (JP) ................................. 2011-060781

(51) Int. Cl.
*C07D 275/04* (2006.01)
(52) U.S. Cl.
USPC ........................................................ 548/209

(58) Field of Classification Search
USPC ........................................................ 548/209
See application file for complete search history.

(56) References Cited

U.S. PATENT DOCUMENTS 5,633,384 A    5/1997    Kagano

FOREIGN PATENT DOCUMENTS

| CN | 101602742 A | 12/2009 |
| JP | H8-134051 | 5/1996 |
| JP | 2002-88072 A1 | 3/2002 |

OTHER PUBLICATIONS

International Search Report for International Application No. PCT/JP2012/054252 dated Apr. 24, 2012.
Office Action dated May 21, 2014 corresponding to Chinese Application No. 201280014176.1 with English Translation.

*Primary Examiner* — Laura L Stockton
(74) *Attorney, Agent, or Firm* — Kratz, Quintos & Hanson, LLP

(57) ABSTRACT

The present invention provides a method for producing 1,2-benzisothiazol-3-one compounds by reacting a 2-(alkylthio)benzonitrile compound with a halogenating agent in the presence of water, the method being characterized in that the reaction proceeds while the halogenating agent and water are gradually and simultaneously added to a reaction system containing the 2-(alkylthio)benzonitrile compound. The invention allows the simple and economical production of highly pure 1,2-benzisothiazol-3-one compounds, which are useful as antimicrobial agents, antifungal agents, etc.

4 Claims, No Drawings

1,2-BENZISOTHIAZOL-3-ONE COMPOUND PRODUCTION METHOD

TECHNICAL FIELD

The present invention relates to a method for producing 1,2-benzisothiazol-3-one compounds useful as antimicrobial agents, antifungal agents, etc.

BACKGROUND ART 1,2-Benzisothiazol-3-one compounds are useful as antimicrobial agents, antifungal agents, etc. Patent Literature 1 listed below discloses a production method therefore comprising reacting a 2-(alkylthio)benzonitrile compound with a halogenating agent in the presence of water. In this method, after mixing a 2-(alkylthio)benzonitrile compound with water, a halogenating agent is added thereto and then reacted. This method achieves a relatively high yield, but there is room for further improvement.

CITATION LIST

Patent Literature

PTL 1: JP8-134051A

SUMMARY OF INVENTION

Technical Problem

A major object of the present invention is to provide a simple and economical method for producing highly pure 1,2-benzisothiazol-3-one compound at a high yield.

Solution to Problem

The present inventors conducted extensive studies to achieve the above object and found that, among methods for producing a 1,2-benzisothiazol-3-one compound by reacting a 2-(alkylthio)benzonitrile compound with a halogenating agent in the presence of water, a method wherein a halogenating agent and water are simultaneously and gradually added to a reaction system that contains a 2-(alkylthio)benzonitrile compound as a starting material to conduct the reaction allows a highly pure 1,2-benzisothiazol-3-one compound to be produced at a high yield while preventing a side reaction and a hydrolysis reaction of the product. The present invention has been accomplished based on this finding.

The present invention provides a method for producing a 1,2-benzisothiazol-3-one compound described below.

Item 1. A method for producing a 1,2-benzisothiazol-3-one compound represented by formula (2):

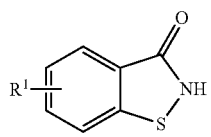

wherein $R^1$ is a hydrogen atom, $C_{1-4}$ alkyl group, $C_{1-4}$ alkoxy group, nitro group, carboxyl group, alkoxycarbonyl group, or halogen atom, the method comprising reacting a 2-(alkylthio)benzonitrile compound represented by formula (1):

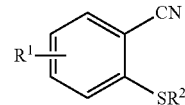

wherein $R^1$ is as defined above and $R^2$ is a $C_{1-4}$ alkyl group, with a halogenating agent in the presence of water, wherein the halogenating agent and water are gradually and simultaneously added to a reaction system containing the 2-(alkylthio)benzonitrile compound to proceed the reaction.

Item 2: The method according to Item 1, wherein the halogenating agent and water are simultaneously added to the reaction system in such a manner that the amount of water added falls within the range of 0.5 times less to 0.5 times more in an amount by mol than the amount by mol of the halogenating agent added to the reaction system.

Item 3: The method for producing a 1,2-benzisothiazol-3-one compound according to Item 1 or 2, wherein the halogenating agent is chlorine or sulfuryl chloride.

The method for producing the 1,2-benzisothiazol-3-one compound of the present invention is explained in detail below.

Starting Material (1) Described below are the groups $R^1$ in the 2-(alkylthio)benzonitrile compound used as the starting material in the present invention and represented by formula (1):

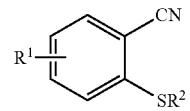

wherein $R^1$ is a hydrogen atom, $C_{1-4}$ alkyl group, $C_{1-4}$ alkoxy group, nitro group, carboxyl group, alkoxycarbonyl group, or halogen atom, and $R^2$ is a $C_{1-4}$ alkyl group. Specifically, examples of $C_{1-4}$ alkyl groups include linear or branched $C_{1-4}$ alkyl groups, such as a methyl group, an ethyl group, an n-propyl group, an isopropyl group, an n-butyl group, an isobutyl group, a sec-butyl group, and a tert-butyl group. Examples of $C_{1-4}$ alkoxy groups include a methoxy group, an ethoxy group, an n-propoxy group, an isopropoxy group, an n-butoxy group, an isobutoxy group, a sec-butoxy group, and a tert-butoxy group. Examples of alkoxycarbonyl groups include those having a $C_{1-4}$ linear or branched alkyl group, such as a methoxycarbonyl group, an ethoxycarbonyl group, a propoxycarbonyl group, and a butoxycarbonyl group. Examples of halogen atoms include a chlorine atom and a bromine atom.

Among these groups or atoms represented by $R^1$, a hydrogen atom, a methyl group, an ethyl group, a tert-butyl group, a methoxy group, a methoxycarbonyl group, an ethoxycarbonyl group, a propoxycarbonyl group, a chlorine atom, a nitro group, and the like are particularly preferable.

Examples of $C_{1-4}$ alkyl groups represented by $R^2$ are the same as those mentioned as the examples of alkyl groups represented by $R^1$. Among these, a methyl group, an ethyl group, an n-propyl group, a tert-butyl group, and the like are preferable.

Specific examples of 2-(alkylthio)benzonitrile compounds represented by formula (1) include 2-(methylthio)benzonitrile, 2-(ethylthio)benzonitrile, 2-(n-propylthio)benzonitrile, 2-(tert-butylthio)benzonitrile, 3-methyl-2-(methylthio)benzonitrile, 5-tert-butyl-2-(methylthio)benzonitrile, 4-methoxy-2-(methylthio)benzonitrile, 3-nitro-2-(methylthio)benzonitrile, 3-nitro-2-(tert-butylthio)benzonitrile, 4-chloro-2-(methylthio)benzonitrile, 4-carboxy-2-(methylthio)benzonitrile, and 4-methoxycarbonyl-2-(methylthio)benzonitrile. Among these, 2-(methylthio)benzonitrile, 3-methyl-2-(methylthio)benzonitrile, 5-tert-butyl-2-(methylthio)benzonitrile, 4-methoxy-2-(methylthio)benzonitrile, 3-nitro-2-(tert-butylthio)benzonitrile, 4-chloro-2-(methylthio)benzonitrile, and 4-methoxycarbonyl-2-(methylthio)benzonitrile are preferable because they are readily available and can render high antimicrobial activity to the product.

In the present invention, any 2-(alkylthio)benzonitrile compound represented by formula (1) produced by any method may be used. For example, it is possible to use a 2-(alkylthio)benzonitrile compound obtained by, as disclosed in Patent Literature 1 (JP8-134051A), reacting a 2-halobenzonitrile compound represented by formula (3):

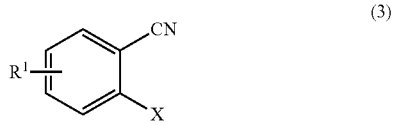

(3)

wherein $R^1$ is the same as $R^1$ in formula (1) and X is a chlorine or bromine atom, with an alkanethiol represented by formula (4):

$R^2SH$ (4)

wherein $R^2$ is the same atom or group as $R^2$ in formula (1), in the presence of a base in a heterogeneous system.

Among the starting materials used in the present invention, examples of usable halogenating agents include chlorine, bromine, sulfuryl chloride, and sulfuryl bromide. Among these, chlorine, and sulfuryl chloride are preferable from an economical viewpoint.

Production Method of 1,2-benzisothiazol-3-one Compound

The method for producing a 1,2-benzisothiazol-3-one compound according to the present invention comprises:

reacting a 2-(alkylthio)benzonitrile compound represented by formula (1):

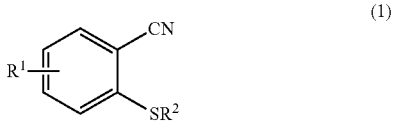

(1)

wherein $R^1$ is a hydrogen atom, $C_{1-4}$ alkyl group, $C_{1-4}$ alkoxy group, nitro group, carboxyl group, alkoxycarbonyl group, or halogen atom, and $R^2$ is a $C_{1-4}$ alkyl group, with a halogenating agent in the presence of water to produce a 1,2-benzisothiazol-3-one compound represented by formula (2):

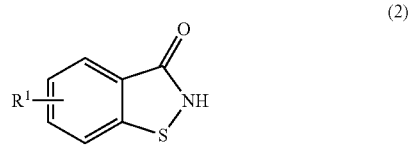

(2)

wherein $R^1$ is the same as defined above.

In this method, the halogenating agent is preferably used in an amount of about 0.8 to 3 mol, and more preferably about 1 to 2 mol, per mol of 2-(alkylthio)benzonitrile compound. When the amount of the halogenating agent is less than the above range, the amount of unreacted 2-(alkylthio)benzonitrile compound tends to increase, and the yield may be undesirably lowered. When the amount of the halogenating agent is unduly large, a side reaction easily occurs and the yield may be lowered.

Water is preferably used in an amount of about 0.8 to 3 mol, and more preferably about 1 to 2 mol, per mol of 2-(alkylthio) benzonitrile compound. When the amount of water falls outside this range, a side reaction easily occurs and the yield may be undesirably lowered.

Water may be used in the form of an aqueous solution of mineral acid by adding a mineral acid to water. Examples of mineral acids include hydrochloric acid, sulfuric acid, and nitric acid. The concentration of the aqueous solution of mineral acid is not particularly limited. In the case of hydrochloric acid, the preferable range generally employed is from 10% by weight to a saturated concentration. In the case of sulfuric acid or nitric acid, 10 to 50% by weight is preferably employed. The addition of mineral acid to water improves selectivity during reaction and suppresses the generation of by-products.

In the method of the present invention, the use of a reaction solvent is not always necessary; however, a reaction solvent may be used if necessary. The use of a reaction solvent can often help the reaction to proceed more smoothly.

The reaction solvent is not particularly limited and any nonaqueous solvent can be used as long as it is inactive to the reaction. Specific examples of such reaction solvents include hydrocarbons, such as n-hexane, cyclohexane, and n-heptane; halogenated hydrocarbons, such as dichloroethane, dichloromethane, and chloroform; aromatic hydrocarbons, such as benzene, toluene, xylene, and monochlorobenzene; N,N-dimethylformamide; dimethyl sulfoxide; and the like. Among these, toluene and monochlorobenzene are preferable.

When a reaction solvent is used, the amount may be generally about 20 to 3,000 parts by mass relative to 100 parts by mass of 2-(alkylthio)benzonitrile compound. When the amount of the reaction solvent is unduly small, the effect of adding the reaction solvent cannot be satisfactorily achieved. When the amount of the reaction solvent is unduly large, the volume efficiency may be undesirably lowered.

The reaction of the 2-(alkylthio)benzonitrile compound represented by formula (1) with a halogenating agent and water is generally conducted at a temperature of about −20 to 170° C., preferably about 0 to 150° C., and more preferably about 20 to 100° C. An unduly low reaction temperature may undesirably slow down the reaction speed and prolong the necessary reaction time. In contrast, an unduly high reaction temperature may easily cause side reactions. Therefore, reaction temperatures that are either unduly low or unduly high are undesirable.

The reaction time depends on the reaction temperature, etc.; however, it is generally about 0.5 to 40 hours.

In the present invention, when a 2-(alkylthio)benzonitrile compound represented by formula (1) is reacted with a halogenating agent under the conditions described above, it is essential to gradually and simultaneously add a halogenating agent and water to a reaction system containing a 2-(alkylthio)benzonitrile compound to proceed the reaction.

By conducting the reaction while gradually and simultaneously adding a halogenating agent and water, the occurrence of a side reaction and a hydrolysis reaction of the product can be suppressed. This makes it possible to obtain, in high purity and at a high yield, the 1,2-benzisothiazol-3-one compound represented by formula (2):

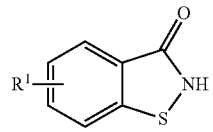

(2)

wherein $R^1$ is the same as defined above.

There is no limitation to the method for adding a halogenating agent and water; however, in order to reduce side reactions and/or hydrolysis reactions so as to maintain a high yield, it is preferable that a halogenating agent and water be added simultaneously in such an amount that both the halogenating agent and water have almost the same amounts by mol. Generally, it is preferable that water be added in an amount that falls within the range of 0.5 times less to 0.5 times more in an amount by mol, more preferably within the range of 0.2 times less to 0.2 times more in an amount by mol, and even more preferably within the range of 0.1 times less to 0.1 times more in an amount by mol, than the amount by mol of the halogenating agent added to the reaction system.

When the amount of water is unduly small relative to the amount of the halogenating agent added, a side reaction easily occurs. In contrast, when the amount of water is unduly large relative to the amount of the halogenating agent added, a decomposition reaction of the product is promoted. Such cases both undesirably lower the yield.

The speed for adding the halogenating agent and water cannot be generalized because it depends on the reaction temperature, etc. The halogenating agent and water may be added continuously or intermittently depending on the specific reaction temperature within the time required to react.

For example, 1/10 or more and preferably 1/2 or more of the total reaction time may be allotted as the time for adding a halogenating agent and water. The halogenating agent and water may be added intermittently or continuously as evenly as possible within this time. More specifically, a halogenating agent and water may be simultaneously and gradually added to the reaction system within the total reaction time. Alternatively, after simultaneously and gradually adding the halogenating agent and water to the reaction system, the mixture may be further heated continuously within the reaction temperature range described above, preferably in a temperature range higher than that at which the halogenating agent and water were added. Note that some water may be contained in the reaction system beforehand within the addable water range. In this case, the amount of water that may be contained in the reaction system in advance may be suitably selected as long as it is about 1 mol or less, preferably about 0.5 mol or less, and more preferably about 0.2 mol or less, per mol of 2-(alkylthio)benzonitrile compound.

The method described above makes it possible to obtain, for example, a highly pure target product (with purity exceeding about 99%) at a high yield of 99% or more depending on the specific reaction conditions and addition conditions.

The 1,2-benzisothiazol-3-one compound thus obtained can be easily isolated and purified, for example, by directly crystallizing from a reaction mixture containing the compound, or extracting and recrystallizing, etc.

Specific examples of the 1,2-benzisothiazol-3-one compounds represented by formula (2), which is the target compound obtained as described above, include 1,2-benzisothiazol-3-one, 7-methyl-1,2-benzisothiazol-3-one, 5-tert-butyl-1,2-benzisothiazol-3-one, 6-methoxy-1,2-benzisothiazol-3-one, 7-nitro-1,2-benzisothiazol-3-one, 6-chloro-1,2-benzisothiazol-3-one, 6-carboxy-1,2-benzisothiazol-3-one, and 6-methoxycarbonyl-1,2-benzisothiazol-3-one.

Advantageous Effects of Invention

The method of the present invention makes it possible to simply and economically produce 1,2-benzisothiazol-3-one compounds, which are useful as antimicrobial agents, antifungal agents, etc., as highly pure compounds at a high yield.

DESCRIPTION OF EMBODIMENTS

The present invention is explained in further detail below with reference to a Production Example, Examples, and a Comparative Example. However, the scope of the present invention is not limited to these Examples.

Production Example 1

Synthesis of 2-(methylthio)benzonitrile

2-Chlorobenzonitrile (27.5 g, 0.2 mol), monochlorobenzene (30.0 g), and a 50% by weight aqueous solution (1.0 g) of tetra-n-butyl ammonium bromide were placed in a 500-ml four-necked flask equipped with a stirrer, a thermometer, a dropping funnel, and a condenser under a nitrogen atmosphere to give a mixture. A 30% by weight aqueous solution (51.4 g) of sodium salt of methanethiol (0.22 mol) was added dropwise to the mixture at 60 to 65° C. over a period of 5 hours under stirring. After completion of the dropwise addition, the mixture was allowed to react at the same temperature for 12 hours.

After completion of the reaction, the reaction mixture was cooled to room temperature. The solvent was distilled off, and then the reaction mixture was distilled under a reduced pressure to give 29.5 g of 2-(methylthio)benzonitrile (boiling point: 139 to 140° C./931 Pa). The yield of the target product relative to 2-chlorobenzonitrile was 99%.

Example 1

2-(Methylthio)benzonitrile (29.8 g, 0.2 mol) obtained in Production Example 1, monochlorobenzene (50.0 g), and water (0.7 g, 0.04 mol) were placed in a 500-ml four-necked flask equipped with a stirrer, a thermometer, and a condenser to give a mixture. Chlorine (15.6 g, 0.22 mol) was blown into the mixture over a period of 2 hours at 45 to 50° C. under stirring. Water (3.6 g, 0.2 mol) was added to the mixture dropwise over a period of 2 hours at the same time with blowing the chlorine. After completion of blowing chlorine and the dropwise addition of water, the mixture was further heated to 65 to 70° C. and then allowed to react for 1 hour.

After completion of the reaction, a 20% by weight aqueous solution (41.0 g) of sodium hydroxide was added thereto at the same temperature, and the mixture was cooled to room temperature. The precipitated crystal was collected by filtration, washed with monochlorobenzene, and dried to obtain 1,2-benzisothiazol-3-one (29.9 g, 0.198 mol). The yield of the target product relative to 2-(methylthio)benzonitrile was 99%. The purity of the obtained 1,2-benzisothiazol-3-one measured with high-performance liquid chromatography was 99.8%.

Example 2

2-Chlorobenzonitrile (27.5 g, 0.2 mol), monochlorobenzene (30.0 g), and a 50% by weight aqueous solution (1.0 g) of tetra-n-butyl ammonium bromide were placed in a 500-ml four-necked flask equipped with a stirrer, a thermometer, a dropping funnel, and a condenser under a nitrogen atmosphere to obtain a mixture. A 30% by weight aqueous solution (51.4 g) of sodium salt of methanethiol (0.22 mol) was added dropwise to the mixture at 60 to 65° C. over a period of 5 hours under stirring. After completion of the dropwise addition, the mixture was further allowed to react at the same temperature for 12 hours. By this operation, 2-(methylthio)benzonitrile was obtained.

After completion of the reaction, the reaction mixture was cooled to room temperature. An organic layer was obtained by liquid separation. Water (0.7 g, 0.04 mol) was added to the resulting organic layer. Chlorine (15.6 g, 0.22 mol) was blown into the organic layer at 45 to 50° C. over a period of 2 hours under stirring. Water (3.6 g, 0.2 mol) was added dropwise thereto over a period of 2 hours at the same time with blowing the chlorine. After completion of blowing chlorine and the dropwise addition of water, the mixture was further heated to 65 to 70° C. and allowed to react for 1 hour.

After completion of the reaction, a 20% by weight aqueous solution (41.0 g) of sodium hydroxide was added at the same temperature and the mixture was cooled to room temperature. The precipitated crystal was collected by filtration, washed with monochlorobenzene, and dried to obtain 1,2-benzisothiazol-3-one (29.9 g, 0.198 mol). The yield of the target product relative to 2-chlorobenzonitrile was 99%. The purity of the obtained 1,2-benzisothiazol-3-one measured with high-performance liquid chromatography was 99.8%.

Example 3

7-Methyl-1,2-benzisothiazol-3-one (31.7 g, 0.192 mol) was prepared in the same manner as in Example 1, except that 3-methyl-2-(ethylthio)benzonitrile (35.4 g, 0.2 mol) was used instead of 2-(methylthio)benzonitrile (29.8 g, 0.2 mol). The yield of the target product relative to 3-methyl-2-(ethylthio)benzonitrile was 96%. The purity of the obtained 7-methyl-1,2-benzisothiazol-3-one measured with high-performance liquid chromatography was 99.6%.

Example 4

5-tert-Butyl-2-(methylthio)benzonitrile (41.0 g, 0.2 mol), monochlorobenzene (50.0 g), and water (0.7 g, 0.04 mol) were placed in a 500-ml four-necked flask equipped with a stirrer, a thermometer, and a condenser to give a mixture. Both sulfuryl chloride (29.7 g, 0.22 mol) and water (3.6 g, 0.2 mol) were simultaneously added dropwise to the mixture over a period of 2 hours at 45 to 50° C. under stirring. After completion of the dropwise addition, the mixture was heated to 65 to 70° C. and allowed to react for 1 hour.

After completion of the reaction, a 20% by weight aqueous solution (41.0 g) of sodium hydroxide was added thereto at the same temperature. The mixture was cooled to room temperature. The precipitated crystal was collected by filtration, washed with monochlorobenzene, and dried to obtain 5-tert-butyl-1,2-benzisothiazol-3-one (40.2 g, 0.194 mol). The yield of the target product relative to 5-tert-butyl-2-(methylthio)benzonitrile was 97%. The purity of the obtained 5-tent-butyl-1,2-benzisothiazol-3-one measured with high-performance liquid chromatography was 99.5%.

Example 5

4-Chloro-2-(methylthio)benzonitrile (36.7 g, 0.2 mol), monochlorobenzene (50.0 g), and 35% by weight hydrochloric acid (1.1 g, water: 0.04 mol) were placed in a 500-ml four-necked flask equipped with a stirrer, a thermometer, and a condenser to give a mixture. Chlorine (15.6 g, 0.22 mol) was blown into the mixture at 45 to 50° C. over a period of 2 hours under stirring and 35% by weight hydrochloric acid (5.5 g, water: 0.2 mol) was added dropwise thereto over a period of 2 hours at the same time with blowing the chlorine. After completion of blowing chlorine and the dropwise addition of water, the mixture was further heated to 65 to 70° C. and allowed to react for 1 hour.

After completion of the reaction, a 20% by weight aqueous solution (41.0 g) of sodium hydroxide was added thereto at the same temperature and the mixture was cooled to room temperature. The precipitated crystal was collected by filtration, washed with monochlorobenzene, and dried to obtain 6-chloro-1,2-benzisothiazol-3-one (36.0 g, 0.194 mol). The yield of the target product relative to 4-chloro-2-(methylthio) benzonitrile was 97%. The purity of the obtained 6-chloro-1,2-benzisothiazol-3-one measured with high-performance liquid chromatography was 99.7%.

Comparative Example 1

2-(Methylthio)benzonitrile (29.8 g, 0.2 mol), monochlorobenzene (50.0 g), and water (4.3 g, water: 0.24 mol) were placed in a 500-ml four-necked flask equipped with a stirrer, a thermometer, and a condenser to give a mixture. Chlorine (15.6 g, 0.22 mol) was blown into the mixture at 45 to 50° C. over a period of 2 hours under stirring. The mixture was further heated to 65 to 70° C. and allowed to react for 1 hour.

After completion of the reaction, a 20% by weight aqueous solution (41.0 g) of sodium hydroxide was added at the same temperature and the mixture was then cooled to room temperature. The precipitated crystal was collected by filtration, washed with monochlorobenzene, and dried to obtain 1,2-benzisothiazol-3-one (29.0 g, 0.192 mol). The yield of the target product relative to 2-(methylthio)benzonitrile was 96%. The purity of the obtained 1,2-benzisothiazol-3-one measured with high-performance liquid chromatography was 97.1%.

The invention claimed is:

1. A method for producing a 1,2-benzisothiazol-3-one compound represented by formula (2):

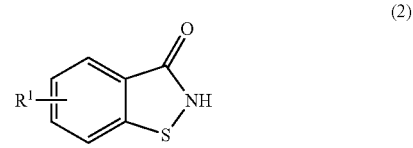

wherein $R^1$ is a hydrogen atom, $C_{1-4}$ alkyl group, $C_{1-4}$ alkoxy group, nitro group, carboxyl group, alkoxycarbonyl group, or halogen atom, the method comprising reacting a 2-(alkylthio)benzonitrile compound represented by formula (1):

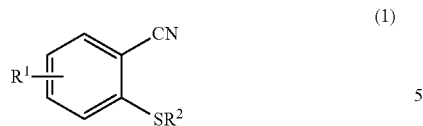

wherein $R^1$ is as defined above and $R^2$ is a $C_{1-4}$ alkyl group, with a halogenating agent in the presence of water, wherein the halogenating agent and water are gradually and simultaneously added to a reaction system containing the 2-(alkylthio)benzonitrile compound to proceed the reaction.

2. The method according to claim 1, wherein the halogenating agent and water are simultaneously added to the reaction system in such a manner that the amount of water added falls within the range of 0.5 times less to 0.5 times more in an amount by mol than the amount by mol of the halogenating agent added to the reaction system.

3. The method for producing a 1,2-benzisothiazol-3-one compound according to claim 1, wherein the halogenating agent is chlorine or sulfuryl chloride.

4. The method for producing a 1,2-benzisothiazol-3-one compound according to claim 2, wherein the halogenating agent is chlorine or sulfuryl chloride.

* * * * *